(12) United States Patent
Landau et al.

(10) Patent No.: US 7,442,182 B2
(45) Date of Patent: Oct. 28, 2008

(54) SPRING POWERED NEEDLE-FREE INJECTION SYSTEM

(75) Inventors: Sergio Landau, Laguna Niguel, CA (US); Christopher Sautter, Portland, OR (US)

(73) Assignee: Bioject, Inc., Tualatin, OR (US)

( * ) Notice: Subject to any disclaimer, the term of this patent is extended or adjusted under 35 U.S.C. 154(b) by 200 days.

(21) Appl. No.: 10/974,004

(22) Filed: Oct. 25, 2004

(65) Prior Publication Data

US 2005/0119608 A1 Jun. 2, 2005

Related U.S. Application Data

(60) Provisional application No. 60/514,025, filed on Oct. 24, 2003.

(51) Int. Cl.
*A61M 5/30* (2006.01)
(52) U.S. Cl. ........................................ 604/68
(58) Field of Classification Search ............ 604/68–72, 604/187, 131, 157, 134–136
See application file for complete search history.

(56) References Cited

U.S. PATENT DOCUMENTS

| | | |
|---|---|---|
| 3,057,349 A | 10/1962 | Ismach |
| 3,129,708 A | 4/1964 | Krantz |
| 3,334,788 A | 8/1967 | Hamilton |
| 3,526,225 A | 9/1970 | Isobe |
| 3,859,996 A | 1/1975 | Mizzy et al. |
| 3,908,651 A | 9/1975 | Fudge |
| 4,103,684 A | 8/1978 | Ismach |
| 4,266,541 A | 5/1981 | Landau |
| 4,342,310 A | 8/1982 | Lindmayer et al. |
| 4,368,731 A | 1/1983 | Schramm |
| 4,592,742 A | 6/1986 | Landau |
| 4,874,367 A | 10/1989 | Edwards |
| 4,913,699 A | 4/1990 | Parsons |
| 4,966,581 A | 10/1990 | Landau |
| 5,062,830 A * | 11/1991 | Dunlap ..................... 604/68 |
| 5,073,165 A | 12/1991 | Edwards |
| 5,312,335 A | 5/1994 | McKinnon et al. |
| 5,334,144 A | 8/1994 | Alchas et al. |
| 5,499,972 A * | 3/1996 | Parsons ..................... 604/68 |
| 5,569,189 A | 10/1996 | Parsons |
| 5,782,802 A | 7/1998 | Landau |
| 6,168,587 B1 | 1/2001 | Bellhouse et al. |
| 6,942,638 B1 * | 9/2005 | Quinn ..................... 604/68 |

FOREIGN PATENT DOCUMENTS

GB    WO95/03844    2/1995

* cited by examiner

*Primary Examiner*—Kevin C. Sirmons
*Assistant Examiner*—Catherine N Witczak
(74) *Attorney, Agent, or Firm*—Kolisch Hartwell, P.C.

(57) ABSTRACT

A needle-free injection device, including a plunger and a spring operatively coupled with the plunger. The plunger is slidably disposed within a fluid chamber, is retractable to draw injectable fluid into the fluid chamber through an injection orifice, and may be advanced within the fluid chamber to forcibly eject injection fluid out through the injection orifice. The spring is configured to be compressed during arming of the injection device, and decompressed during discharge to forcibly advance the plunger within the fluid chamber. The injection device further includes an actuator operable to cause the spring to be compressed during arming of the injection device, and selectively operable prior to decompression of the spring to cause the plunger to be moved to a desired position within the fluid chamber.

22 Claims, 3 Drawing Sheets

SPRING POWERED NEEDLE-FREE INJECTION SYSTEM

CROSS-REFERENCE TO PRIORITY APPLICATION

This application is based upon and claims the benefit under 35 U.S.C. § 119(e) of the following U.S. provisional patent application, which is incorporated herein by reference in its entirety for all purposes: Ser. No. 60/514,025, filed Oct. 24, 2003.

BACKGROUND

Needle-free injection systems provide an alternative to standard fluid delivery systems, which typically use a needle adapted to penetrate the outer surface of an injection site. Typically, needle-free injection systems are designed to eject the fluid from a fluid chamber with sufficient pressure to allow the fluid to penetrate the target to the desired degree. For example, common applications for needle-free injection systems include delivering intradermal, subcutaneous and intramuscular injections into or through a recipient's skin. For each of these applications, the fluid must be ejected from the system with sufficient pressure to allow the fluid to penetrate the tough exterior dermal layers of the recipient's skin.

DETAILED DESCRIPTION

Figure 1:
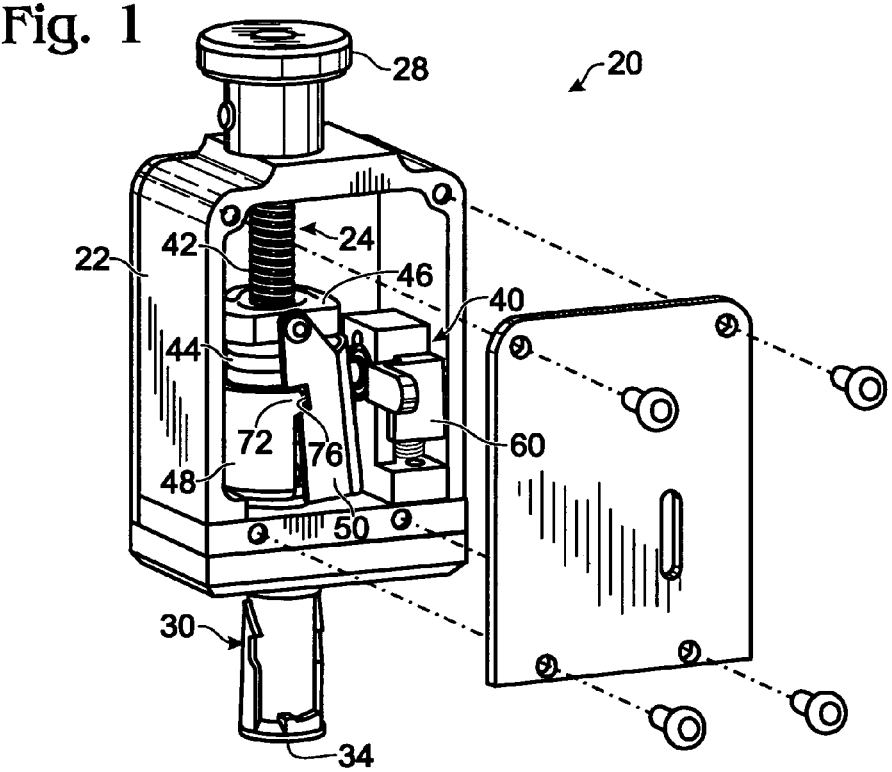
FIG. 1 is an isometric view of a needle-free injection device according to the present description.
Figure 3:
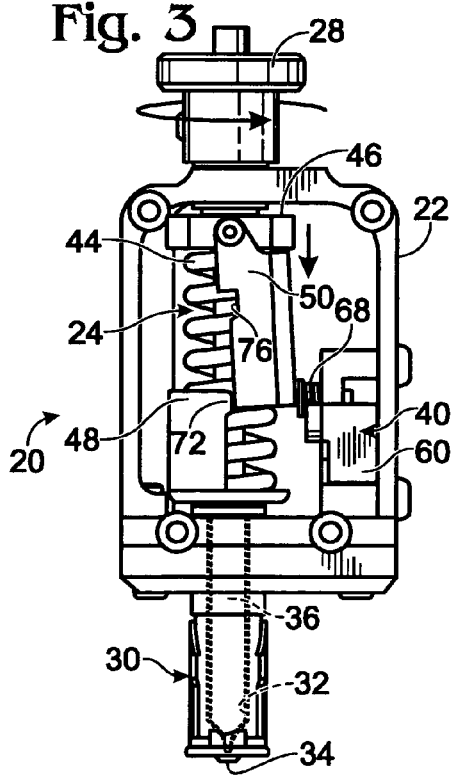
FIGS. 3-8 are various side view depictions of the injection device of FIGS. 1 and 2, depicting further aspects of the injection device and its operation.
Figure 2:
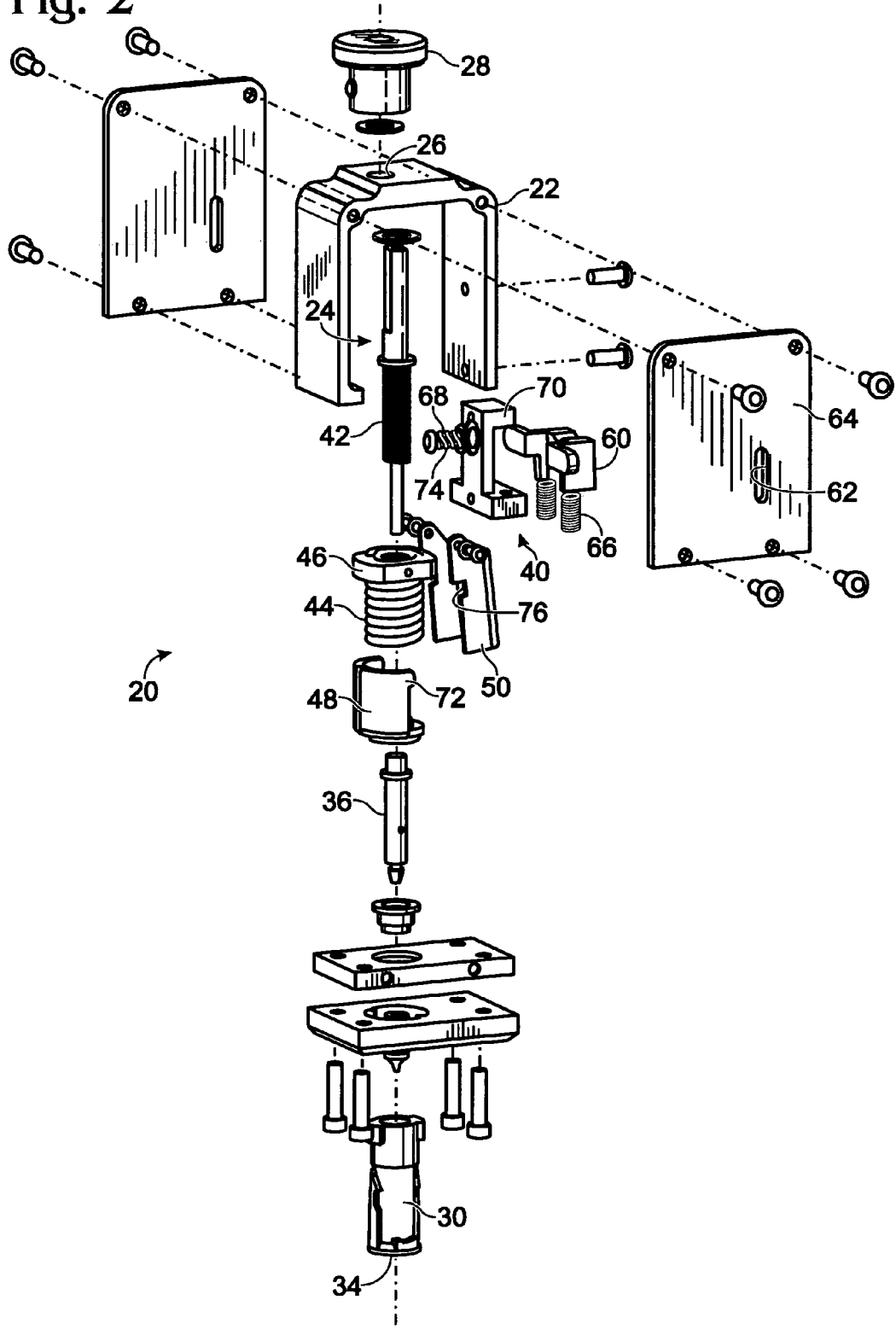
FIG. 2 is an isometric exploded view of the injection device of FIG. 1.

FIGS. 1-8 variously depict a needle-free injection device 20 according to the present description. Referring first to FIGS. 1-3, various component parts of the exemplary injection device will be described, and then various references to the FIGS. 1-8 will be used to describe operation of the device. As shown, injection device 20 may include a housing 22. Though the depicted example has a rectangular housing, various other shapes may be employed as desired.

An elongate shaft 24 extends through an opening 26 in housing 22. Typically, opening 26 and/or shaft 24 is configured so that the shaft is prevented from moving linearly (e.g., sliding lengthwise) through the hole, while being permitted to freely rotate about the long axis of the shaft. An actuator, such as knob 28, is mounted to shaft, to enable a user to selectively rotate shaft 24 in either a clockwise or counterclockwise direction.

A nozzle 30 is secured to housing 22 generally opposite knob 28. A fluid chamber 32 is defined within nozzle 30, and is fluidly coupled with an injection orifice 34. A plunger 36 is slidably disposed within fluid chamber 32. Plunger 36 may be retracted within fluid chamber 32 to cause injectable fluid to be drawn into the fluid chamber. Plunger 36 may then be forcibly advanced within fluid chamber 32 to cause injectable fluid to be forcibly ejected out injection orifice 34 (e.g., into a patient's skin or other injection site).

Injection device 20 may be configured to be reused for multiple injections. With some such multiple-use embodiments, it may be desirable to periodically replace the nozzle with a fresh unused nozzle, to reduce contamination risks. The nozzle may be replaced, for example, after every injection or after a set number of injections.

A triggering mechanism 40 may be provided on housing 22. As explained in more detail below, once injection device is armed, triggering mechanism 40 may be operated to cause the injection device to discharge, so as to forcibly eject fluid from injection orifice 34.

Housing 22 typically has a hollow interior containing various components. Shaft 24 extends into the interior of the housing, and may include a threaded portion 42. In many cases, it will be desirable that shaft extend through substantially the entire interior of housing 22. A spring 44 is disposed within the housing interior, with elongate shaft 24 extending through the coils of the spring, such that the spring is oriented to compress and decompress in a direction aligned with the long axis of the shaft 24.

Spring 44 may be disposed between spring stops 46 and 48, such that bringing the stops closer together compresses the spring, while decompression of the spring pushes the stops farther apart. Stops 46 and 48 may also be referred to as compressors, due to the role they play in compressing the spring and maintaining it in a compressed state prior to discharge of the device. Stop 48 may also be referred to as the proximal spring stop, because it is closer than the other stop to injection orifice 34, and thus to the injection site. Because stop 46 is further from the injection site, it may be referred to as the distal spring stop.

Distal spring stop 46 is threadably engaged with threaded portion 42 of elongate shaft 24, such that rotation of the shaft causes distal spring stop 46 to move back and forth within housing 22. The general range of movement of the distal spring stop is from the distal end of the housing interior (i.e., the housing wall closest to knob 28) to about halfway through the interior of the housing, as will be appreciated by noting the length of the threaded portion of shaft 24. Proximal spring stop 48, like distal spring stop 46, may be configured to surround a portion of shaft 24, though the proximal spring stop is not threadably engaged with the shaft. Thus, the shaft need not be rotated for proximal spring stop 48 to move along the shaft within the interior of housing 22. Indeed, depending upon the selected injection volume, as will be explained, the proximal spring stop may move within housing 22 from a proximal end of the housing (i.e., closest to nozzle 30) to approximately halfway through the housing.

Proximal spring stop 48 is attached to, or formed integrally with, plunger 36, such that when the proximal spring stop moves within housing 22, the plunger moves along with it. For example, movement of the proximal spring stop toward the distal side of housing 22 results in plunger 36 retracting within fluid chamber 32, so as to draw fluid in through injection orifice 34, as will be explained in more detail below.

Though proximal spring stop 48 typically is not threaded to shaft 34, various other constraints and forces may govern its movement. For example, spring 44 urges the spring stops apart. Because the distal spring stop 46 is held in place (linearly) via its threaded engagement with shaft 24, the spring force tends to push the proximal stop until it bottoms out and abuts the proximal interior wall of housing 22 (i.e., the interior housing wall adjacent nozzle 30).

In addition, a latch or other mechanism or device may be provided to fix the distance between the distal spring stop and proximal spring stop. For example, the depicted exemplary embodiment includes a latch 50 pivotally connected to distal spring stop 46. As explained in more detail below, shaft 24 may be rotated to a point where the distal spring stop advances within the housing sufficiently far enough toward proximal spring stop 48 to allow them to be coupled together via latch 50. When the spring stops are thus coupled together, rotation of shaft 24 in an opposite direction may be employed to retract both spring stops in a distal direction within housing 22. As explained above, this retraction of the proximal spring stop will cause plunger 36 to retract within fluid chamber 32 to load injectable fluid into the device. Once the plunger is withdrawn by a desired amount, the injection orifice may be positioned near an injection site to ready the injection. The injection is then administered by releasing latch 50 (e.g., by operating triggering mechanism 40), so as to permit spring 44 to decompress and forcibly advance proximal spring stop 48 and plunger 36.

Triggering mechanism 40 may include a trigger 60 that is exposed and that extends through an opening or slot 62 in housing wall 64. A trigger spring or springs 66 may be provided to bias trigger 60 in a desired direction, as will be explained. The triggering mechanism may also include a post 68 slidably disposed within a post guide 70 and oriented to extend inward into the interior of housing 22 in a direction generally perpendicular to shaft 24. As will be explained below, the components of triggering mechanism 40 may be configured to urge latch 50 into a position in which it operatively couples the distal and proximal spring stops. Once the stops are coupled, the triggering mechanism maintains the latch in place until actuation of trigger 60, which causes release of the latch, which in turn initiates decompression of spring 44 and delivery of the injection. Operation of triggering mechanism 40 and its interaction with latch 50 will be further explained with reference to FIGS. 3-8.

Referring now to FIG. 3, injection device is shown in a disarmed condition, in which spring 44 is relatively decompressed. Distal spring stop 46 is in its furthest distal position adjacent the distal end of the interior of housing 22. Proximal spring stop 48 is in its furthest proximal position adjacent the proximal end of the housing. Plunger 36 is thus fully advanced within fluid chamber 32, such that little or no injectable fluid is in fluid chamber 32. A tab or protrusion 72 on proximal spring stop 48 bears against latch 50, forcing it into an outward pivoted position in which the proximal end of the latch is pivoted away from shaft 24. In this outward pivoted position, latch 50 holds post 68 laterally outward against the force of post spring 74. When post 68 is pushed outward into this position, it blocks trigger 60, preventing the trigger from being moved distally (i.e., upward in the figure) by the urging force of trigger spring 66.

Figure 4:
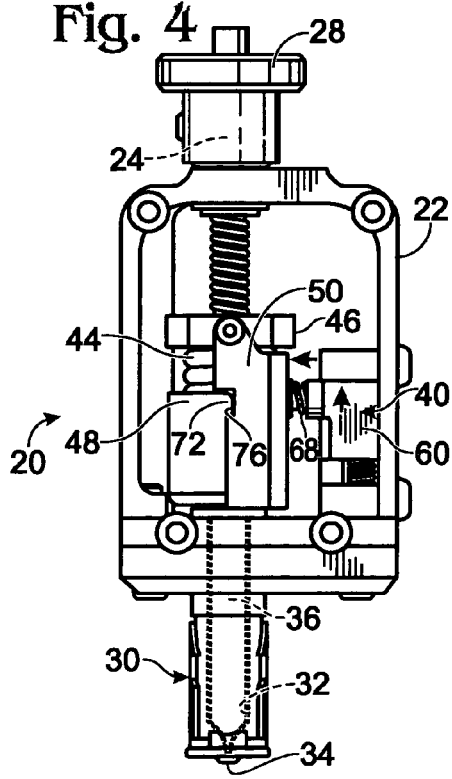

Referring still to FIG. 3, the figure shows knob 28 being rotated in a counterclockwise direction. Due to the threaded engagement of distal spring stop 46 with shaft 24, this rotation causes proximal movement (i.e., downward in the figure) of the distal spring stop 46, as indicated by the arrow. Continued rotation of shaft 24 causes distal spring stop 46 to continue moving proximally, compressing spring 44, until the position shown in FIG. 4 is reached. At this point, spring 44 is fully compressed. Also, the spring stops have been brought sufficiently close together so that tab 72 on proximal spring stop 48 aligns with a recess 76 on latch 50. This alignment of tab 72 and recess 76 allows the latch to pivot inward toward shaft 24, as a result of post spring 74 urging post 68 inward against latch 50. As latch 50 pivots inward, post 68 moves laterally inward so that it no longer blocks distal motion of trigger 60. Trigger spring 66 thus causes trigger 60 to move upward. Once trigger 60 has moved upward (FIG. 4), it occupies a position in which it blocks post 68 from moving outward back to its original position.

Figure 5:
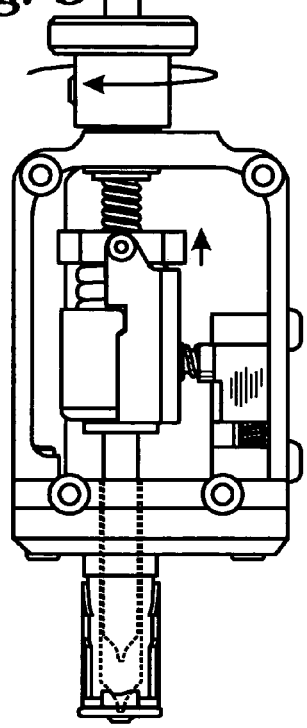

Referring now to FIG. 5, knob 28 may be rotated clockwise (opposite the earlier rotation), to withdraw distal spring stop 46 and move it distally within housing 22. Recess 76 and tab 72 interact to link the spring stops together, so that proximal spring stop 48 is retracted along with distal spring stop 46 upon clockwise rotation of shaft 24. Tab 72 and/or recess 76 may be provided with a sloped profile, such that the force of spring 44 tends to cause latch 50 to pivot outward, thereby de-latching the spring stops, absent a counteracting force. As previously indicated, post 68 is prevented by trigger 60 from moving back outward, such that the post provides this counteracting force, and holds latch 50 in the inward non-pivoted position. Post 68 continues blocking latch 50 against outward pivoting until the user operates trigger 60 to unblock post 68, which in turn allows the latch to pivot outward, which in turn unlatches the spring stops to allow spring 44 to decompress and discharge the device.

Figure 6:
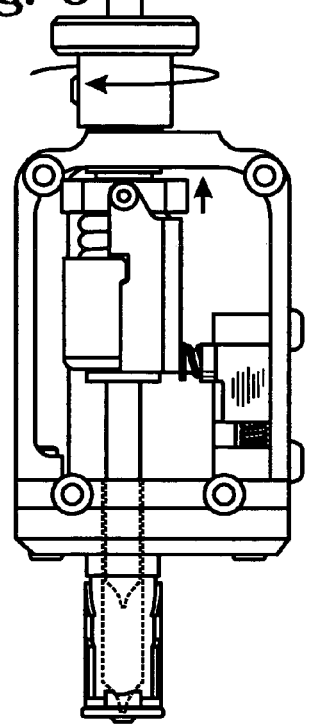

Referring still to FIG. 5, knob 28 is rotated clockwise until a desired amount of retraction is achieved. It will thus be appreciated that the knob not only controls arming of the device, but also may be used to selectively vary the volume or dose of injectable fluid to be injected. FIG. 6 shows the device fully retracted, though it will be appreciated that lesser retraction may be employed for lower volume injections. Prior to retraction of plunger 36, nozzle 30 may be coupled with a vial, bottle or other external supply of injectable fluid, such that upon retraction of plunger 36, a dose of injectable fluid is drawn into fluid chamber 32.

Figure 7:
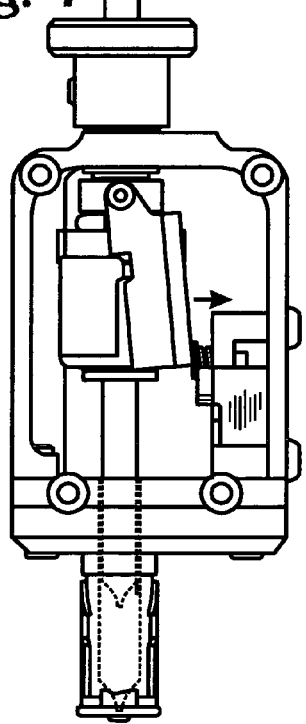
Figure 8:
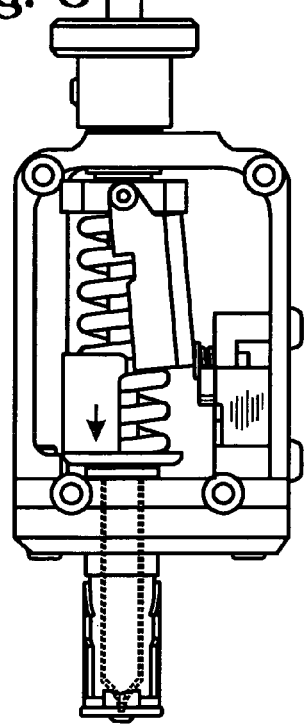

In any case, once the desired retraction is achieved (and after decoupling of any external supply of fluid), injection orifice 34 is placed on the injection site and triggering mechanism 40 is actuated by the user to deliver the injection. Specifically, the user slides trigger 60 so as to move it out of the position in which it blocks post 68. Upon actuation of trigger 60, the force of spring 44 and the sloped profile of tab 72 and/or recess 76 cause latch 50 to pivot outward, as shown in FIG. 7, causing post 68 to move outward and return to its original position (i.e., the position described with reference to FIG. 3). Proximal spring stop 48 and plunger 36 then advance, causing injectable fluid to be forcibly ejected from injection orifice 34, until the proximal spring stop bottoms out on the proximal interior wall of housing 22, as shown in FIG. 8, corresponding to full advancement of plunger 36.

As discussed above, it will be desirable in some embodiments that the injection device be configured for multiple uses. To reuse the device, the above steps may be repeated to deliver additional injections, with fresh unused nozzle assemblies being used as desired to reduce contamination risks.

While various alternative embodiments and arrangements of a needle-free injection device and method have been shown and described above, it will be appreciated that numerous other embodiments, arrangements, and modifications are possible and are within the scope of the invention. The foregoing description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

What is claimed is:

1. A needle-free injection device, comprising:
    a housing;
    an elongate shaft;
    a first spring stop member;
    a second spring stop member, where one of the first and second spring stop members is threadably engaged with a threaded portion of the shaft;

a spring disposed between the first and second spring stop members; and a plunger secured to the second spring stop member and slidably disposed within a fluid chamber, the plunger being operable to be retracted to draw injectable fluid into the fluid chamber through an injection orifice, and advanced within the fluid chamber to cause the injectable fluid to be forcibly ejected out through the injection orifice, where the injection device is configured so that, when the injection device is in an unarmed condition, and upon rotation of the shaft in a first direction, the first and second spring stop members are brought closer together to compress the spring, where the injection device includes a latching mechanism configured to latch the first and second spring stop members together upon full compression of the spring, so as to maintain the spring in a fully compressed state between the first and second spring stop members, where the latching mechanism includes a latch member that is pivotally connected to one of the first and second spring stop member and configured to move through the housing when the one of the first and second spring stop member moves through the housing, and where, when the first and second spring stop members are latched together, the first and second spring stop members are configured for movement through the housing while maintaining the spring in a fully compressed state.

2. The injection device of claim 1, further comprising a triggering mechanism selectively operable to cause the latching mechanism to release and thereby unlatch the first and second spring stop members.

3. The injection device of claim 1, where the injection device is further configured so that, after full compression of the spring and latching of the first and second spring stop members has been achieved, the shaft is rotatable to vary how far the plunger is retracted within the fluid chamber prior to delivery of the injection, to thereby enable adjustment of injection volume.

4. The injection device of claim 1, where the first spring stop member is thread ably engaged with the threaded portion of the shaft and is configured to move through the housing as it moves along the threaded portion.

5. The injection device of claim 4, where the first and second spring stop members are disposed within the housing, and where when the injection device is in the unarmed condition, and upon rotation of the shaft in the first direction, the first spring stop member moves within the housing toward the second spring stop member.

6. The injection device of claim 5, where the injection device is configured so that during rotation of the shaft in the first direction prior to latching together of the first and second spring stop members, the second spring stop member remains stationary relative to the housing, and where the injection device is further configured so that, after latching of the first and second spring stop members together, rotation of the shaft in a second direction causes the first and second spring stop members to together move within the housing, and retract the plunger within the fluid chamber.

7. The injection device of claim 1, where the latching mechanism is configured to automatically latch the first and second spring stop members together upon the spring being compressed to a predetermined level.

8. The injection device of claim 7, where the latching mechanism is biased to latch the first and second spring stop members together.

9. The injection device of claim 8, further comprising a spring configured to urge the latch member that is pivotally connected to one of the first and second spring stop members to pivot towards the other of the first and second spring stop members.

10. The injection device of claim 1, where the latch member is pivotally connected to the first spring stop member and configured to move through the housing when the first spring stop member moves through the housing.

11. The injection device of claim 10, where the latch member is configured to engage the second spring stop member to latch the first and second spring stop members together.

12. The injection device of claim 11, where the latch member includes a recess configured to engage the second spring stop member.

13. A needle-free injection device, comprising:
a plunger slidably disposed within a fluid chamber, the plunger being operable to be retracted to draw injectable fluid into the fluid chamber through an injection orifice, and advanced within the fluid chamber to cause the injectable fluid to be-forcibly ejected out through the injection orifice;

a spring operatively coupled with the plunger and configured to be compressed during arming of the injection device, the spring being further configured to decompress and thereby forcibly advance the plunger within the fluid chamber;

an actuator operable to cause the spring to be compressed during arming of the injection device, and selectively operable prior to decompression of the spring to cause the plunger to be moved to a desired position within the fluid chamber; and a pivotal latching mechanism configured to move through the injection device as the spring is compressed, where the pivotal latching mechanism is biased to maintain the spring in a compressed state during retraction of the plunger, and where the pivotal latching mechanism and the spring in its compressed state together move through the injection device during the retraction of the plunger.

14. The injection device of claim 13, where the spring is disposed between a first spring stop member and a second spring stop member, the plunger being secured to the second spring stop member, where one of the first and second spring stop members is threadably engaged with a shaft to which the actuator is secured, and where when the injection device is in an unarmed condition, and upon rotation of the shaft in a first direction, the first and second spring stop members are brought closer together to compress the spring therebetween.

15. The injection device of claim 14, where the first spring stop member is threadably engaged with the shaft.

16. The injection device of claim 15, where the first and second spring stop members are disposed within a housing, the latching mechanism includes a latch member that is pivotally connected to the first spring stop member, and where when the injection device is in the unarmed condition, and upon rotation of the shaft in the first direction, the first spring stop member and the latch member moves within the housing toward the second spring stop member.

17. The injection device of claim 16, further comprising a latching mechanism configured to latch the first and second spring stop members together upon full compression of the spring to maintain the spring in a fully compressed state, and where prior to such latching of the first and second spring stop members, the second spring stop member remains stationary relative to the housing, the injection device being further configured so that, after latching together of the first and second spring stop members, rotation of the shaft in a second direction causes the first and second spring stop members to together move within the housing and retract the plunger within the fluid chamber.

18. The injection device of claim 14, further comprising latching mechanism configured to latch the first and second spring stop members together upon full compression of the spring, so as to maintain the spring in a fully compressed state between the first and second spring stop members.

19. The injection device of claim 18, further comprising a triggering mechanism selectively operable to cause the latching mechanism to release and thereby unlatch the first and second spring stop members.

20. The injection device of claim 18, where the latching mechanism maintains the spring in the fully compressed state while the pivotal latching mechanism and the spring in the fully compressed state move through the injection device during retraction of the plunger.

21. The injection device of claim 14, where the latching mechanism includes a recess configured to latch the first and second spring stop members together.

22. The injection device of claim 21, where one of the first and second spring stop members includes a protrusion configured to couple with the recess in the latching mechanism of the other of the first and second spring stop members.

* * * * *